United States Patent [19]

Yale et al.

[11] 3,984,421

[45] Oct. 5, 1976

[54] DERIVATIVES OF [[(1-PIPERIDINYL)ETHYL]PHENYL]ALKANEDIAMINES

[75] Inventors: Harry L. Yale, New Brunswick; James A. Bristol, Boonton, both of N.J.

[73] Assignee: E. R. Squibb & Sons, Inc., Princeton, N.J.

[22] Filed: May 8, 1975

[21] Appl. No.: 575,674

[52] U.S. Cl............. 260/293.79; 260/293.73
[51] Int. Cl.².................................. C07D 295/12
[58] Field of Search............. 260/293.73, 293.79

[56] References Cited
UNITED STATES PATENTS

| | | | |
|---|---|---|---|
| 2,626,948 | 1/1953 | Finkelstein et al. | 260/293.79 |
| 3,536,712 | 10/1970 | Keck et al. | 260/293.79 |

OTHER PUBLICATIONS

Kindler et al., e.a. 45:1970 g (1951).

*Primary Examiner*—Norma S. Milestone
*Attorney, Agent, or Firm*—Lawrence S. Levinson; Merle J. Smith; Donald J. Barrack

[57] ABSTRACT

Compounds of the formula

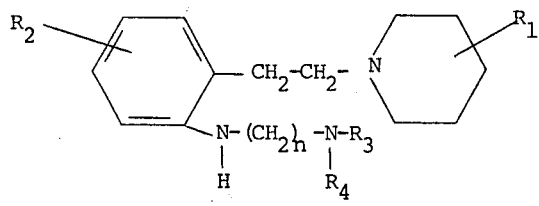

and pharmaceutically acceptable salts alkylthio, wherein $R_1$ is hydrogen, halogen, alkyl, alkoxy, alkythio, benzyl, phenylethyl, phenyl, phenylthio, or phenyl mono-substituted with a halogen, an alkyl group, an alkoxy group or a trifluoromethyl group; $R_2$ is hydrogen, Halogen, alkyl, alkoxy, alkylthio, alkylsulfonyl, phenyl phenyloxy, sulfamoyl, dialkylamidosulfonyl, trifluoromethyl or phenyl or phenyloxy mono-substituted with a halogen, an alkyl group, an alkoxy group or a trifluoromethyl group; $R_3$ is hydrogen, alkyl or or hydroxyalkyl; and $n$ is 2, 3 or 4 are useful as central nervous system depressants.

8 Claims, No Drawings

DERIVATIVES OF [[(1-PIPERIDINYL)ETHYL]PHENYL]ALKANEDIAMINES

SUMMARY OF THE INVENTION

Compounds having the formula

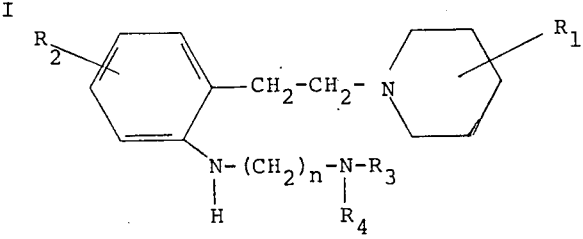

and pharmaceutically acceptable salts thereof, are useful central nervous system depressants. In formula I, and throughout the specification, the symbols are as defined below:

$R_1$ is hydrogen, halogen, alkyl, alkoxy, alkylthio, benzyl, phenylethyl, phenyl, phenylthio, or phenyl mono-substituted with alkyl, alkoxy, or trifluoromethyl;

$R_2$ is hydrogen, halogen, alkyl, alkoxy, alkylthio, alkylsulfonyl, phenyl, phenyloxy, sulfamoyl, dialkylamidosulfonyl, trifluoromethyl, or phenyl or phenyloxy mono-substituted with halogen, alkyl, alkoxy, or trifluoromethyl;

$R_3$ is hydrogen, alkyl or hydroxyalkyl;

$R_4$ is alkyl or hydroxyalkyl; and $n$ is 2, 3 or 4.

The term "alkyl" as used throughout the specification refers to straight or branched chain alkyl groups having 1 to 4 carbon atoms, e.g., methyl, ethyl, propyl, isopropyl, butyl, t-butyl, etc. Those alkyl groups having 1 to 3 carbon atoms are preferred.

The term "alkoxy" as used throughout the specification refers to groups having the formula Y—O— wherein Y is alkyl as defined above. Alkoxy groups having 1 to 3 carbon atoms are preferred.

The term "halogen" as used throughout the specification refers to fluorine, chlorine, bromine and iodine. Chlorine and bromine are the preferred halogens.

DETAILED DESCRIPTION OF THE INVENTION

The compounds of formula I are prepared from 11,12-dihydropyrido[2,1-b][1,3]benzodiazepines having the formula:

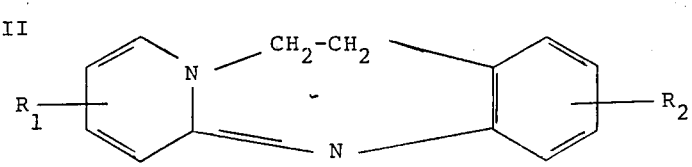

These compounds are known; see Yale et al., U.S. Pat. No. 3,825,549 issued July 23, 1974, the disclosure of which is incorporated herein by reference.

The compounds of formula II can be reduced, using procedures well known in the art. The compounds undergo hydrogenolysis to yield compounds having the formula:

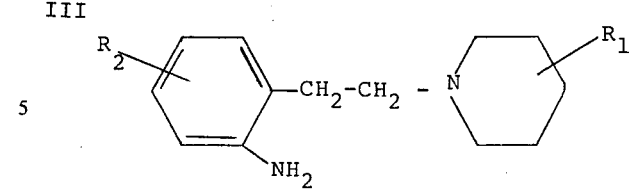

The reaction can be carried out in an organic solvent, preferably a lower alkanol such as methanol, using a catalyst such as platinum oxide or Raney nickel and gaseous hydrogen. The intermediates of formula III, are novel, and as such they constitute a part of this invention.

The alkylation of a compound of formula III can be carried out by either of two alternative processes. Reaction of a compound of formula III with an appropriate base, e.g., sodium hydride or thallous ethoxide, yields a salt having the structure:

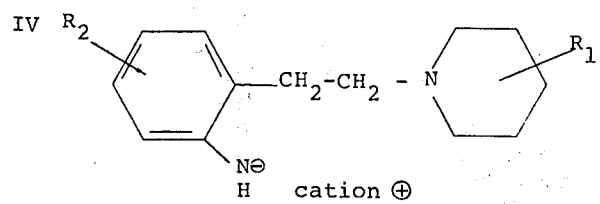

The reaction can be run in an inert polar solvent, e.g., dimethylsulfoxide or dimethylformamide. Reaction conditions are not critical, and the reaction can be run at room temperature for a period of from 1 minute to several hours. The salt of formula IV is subsequently reacted with a compound having the formula:

$$R_3R_4-N-(CH_2)_n-X \qquad V$$

wherein X is chlorine, bromine, alkylsulfonate (e.g., methanesulfonate) or arylsulfonate (e.g., toluenesulfonate) to obtain a compound of formula I.

Alternatively, the alkylation of a compound of formula III can be accomplished by first reacting the piperidine derivative with a compound having the formula $$Cl-(CH_2)_n-Br \qquad VI$$

to yield a compound having the structure

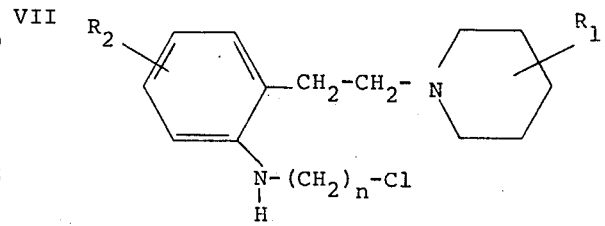

The reaction can be run in an organic solvent, preferably tetrahydrofuran or methyl ethyl ketone in the presence of a base such as sodium hydride or sodium hydroxide. Reaction conditions are not critical, but the reaction will preferably be run under reflux conditions for about 6 hours to 24 hours. The products of formula I can be formed by reacting a compound of formula VII with an amine having the structure $R_3R_4NH$           VIII The reaction can be run neat or in an organic solvent such as toluene. Reaction conditions are not critical and the reaction can be run at room temperature or at elevated temperatures.

The novel piperidine derivatives of formula I can be converted, using procedures well known in the art, into their pharmaceutically acceptable acid-addition salts. Illustrative of the salts contemplated for use in this invention are the hydrohalides (e.g., the hydrochloride and hydrobromide), sulfate, nitrate, tartrate, phosphate, maleate, fumarate, citrate, succinate, methanesulfonate, benzenesulfonate, toluenesulfonate, and the like.

The compounds of formula I, and the pharmaceutically acceptable acid-addition salts thereof, are useful in mammalian species such as rats, dogs, monkeys and others, as central nervous system depressants, and can be used as tranquilizers for the relief of anxiety and tension states in the same manner as chlordiazepoxide. For this purpose these compounds can be incorporated in a conventional dosage form such as tablet, capsule, injectable or the like, along with the necessary carrier material, excipient, lubricant, buffer or the like, for oral or parenteral administration in single or divided doses of about 1 to 100 mg/kg/day, preferably about 5 to 15 mg/kg, two to four times daily.

The following examples are specific embodiments of this invention.

EXAMPLE 1

1,1-Dimethyl-3-[2-[2-(1-piperidinyl)ethyl]phenyl]-1,3-propanediamine

A. 1-[2-(2-Aminophenyl)ethyl]piperidine

Platinum oxide catalyst (1.0 g) is added to a solution of 11,12-dihydropyrido[2,1-b][1,3]benzodiazepine (20.0 g) in methanol (550 ml). Hydrogen gas (about 50 psig) is added and hydrogen uptake is completed in about 1 and 2 hours. The catalyst is filtered off, and the filtrate is concentrated to yield 22.0 g of material that crystallizes spontaneously, melting point 36°–38° C. Recrystallization from 150 ml of pentane yields 16.0 g of the title compound, melting point 39°–41° C.

B. 1,1-Dimethyl-3-[2-[2-(1-piperidinyl)ethyl]phenyl]-1,3-propanediamine

To a solution of 1-[2-(2-aminophenyl)ethyl]piperidine (4.5 g) in anhydrous dimethylsulfoxide (18 ml) under a nitrogen blanket is added 1.2 g of 50% sodium hydride in mineral oil over a 30 minute period, with stirring, at 20° C. Following completion of the addition, the mixture is stirred for 2 hours at 20° C, and then treated with 3-(dimethylamino)propyl chloride (6.0 g) dropwise. Stirring is continued for 2 hours at 20° C and for an additional 2 hours at 40° C, followed by cooling and the addition of 2 ml of absolute ethanol. The reaction mixture is partitioned between 500 ml of water and 100 ml of ether. The aqueous phase is extracted successively with two 100 ml portions of ether, and the combined ether extracts are washed with water. The washed ether solution is reextracted with three 50 ml portions of cold 5% aqueous hydrochloric acid. The combined acid extracts are washed with ether, cooled, and treated with an excess of aqueous sodium hydroxide. The oil that separates is recovered by ether extraction to yield 5.40 g of the title compound, boiling point 200°–205° C (at 0.01 mm of Hg).

EXAMPLE 2

1,1-Dimethyl-3-[2-[2-(1-piperidinyl)ethyl]phenyl]-1,3-propanediamine, oxalate salt (1:1)

To a solution of 1,1-dimethyl-3-[2-[2-(1-piperidinyl)ethyl]phenyl]-1,3-propanediamine (2.1g) in 50 ml of 2-propanol is added 2.0g of oxalic acid in 25 ml of 2-propanol. The precipitate that forms is filtered, dissolved in 20 ml of methanol, and 40 ml of chloroform is added. The solution is then concentrated to 50 ml and the solution cooled; a fine crystalline mass is deposited. Recrystallization from methanol-chloroform (1:2) yields the title compound, melting point 101°–102° C.

EXAMPLE 3

1,1-Dimethyl-2-[2-[2-(1-piperidinyl)ethyl]phenyl]-1,2-ethanediamine

Following the procedure of Example 1, but utilizing in Part B 4.1g of 1-[2-(2-aminophenyl)ethyl]piperidine, 20 ml of dimethylsulfoxide and 2.0g of 50% sodium hydride in mineral oil, and substituting 4.3g of 2-(dimethylamino)ethyl chloride for 3-(dimethylamino)propyl chloride yields 5.25g of the title compound, boiling point 195°–197° C (at 0.2 mm of Hg).

EXAMPLE 4

1,1-Dimethyl-2-[2-[2-(1-piperidinyl)ethyl]phenyl]-1,2-ethanediamine, dihydrochloride To a solution of 1,1-dimethyl-2-[2-[2-(1-piperidinyl)ethyl]phenyl]-1,2-ethanediamine (2.7g) prepared as described in Example 3 in dry ether (50 ml) is added, with stirring and cooling, 10 ml of N ethereal hydrogen chloride solution, dropwise; the title compound separates out.

EXAMPLES 5–46

Following the procedure of Example 1, but substituting the compound in column I below for 11,12-dihydropyrido[2,1-b][1,3]benzodiazepine and the compound listed in column II below for 3-(dimethylamino)propyl chloride, the compound listed in column III below is obtained.

| Example | Column I | Column II | Column III |
|---|---|---|---|
| 5 | 3-chloro-11,12-dihydro-pyrido[2,1-b][1,3]benzodiazepine | 3-(methylamino)propyl chloride | 1-methyl-3-[4-chloro-2-[2-(1-piperidinyl)ethyl]phenyl]-1,3-propanediamine |
| 6 | 3-(methoxy)-11,12-dihydro-pyrido[2,1-b][1,3]benzodiazepine | 2-(diisopropylamino)-ethyl chloride | 1,1-diisopropyl-2-[4-(methoxy)-2-[2-(1-piperidinyl)ethyl]phenyl]-1,2-ethanediamine |
| 7 | 3-ethyl-11,12-dihydro-pyrido[2,1-b][1,3]benzodiazepine | 2-(dimethylamino)-ethyl chloride | 1,1-dimethyl-2-[4-ethyl-2-[2-(1-piperidinyl)ethyl]phenyl]-1,2-ethanediamine |
| 8 | 4-(methylsulfonyl)-11,12- | 2-(2-hydroxyethyl- | 1-(2-hydroxyethyl)-2-[3-(methyl- |

| Example | Column I | Column II | Column III |
|---|---|---|---|
| | dihydropyrido[2,1-b][1,3]benzodiazepine | amino)ethyl chloride | sulfonyl)-2-[2-(1-piperidinyl)ethyl]phenyl]-1,2-ethanediamine |
| 9 | 3-(phenyloxy)-11,12-dihydropyrido[2,1-b][1,3]-benzodiazepine | 4-(methylamino)-butyl chloride | 1-methyl-4-[4-(phenyloxy)-2-[2-(1-piperidinyl)ethyl]phenyl]-1,4-butanediamine |
| 10 | 2-(ethoxy)-11,12-dihydropyrido[2,1-b][1,3]-benzodiazepine | 2-(butylamino)ethyl chloride | 1-butyl-2-[5-(ethoxy)-2-[2-(1-piperidinyl)ethyl]phenyl]-1,2-ethanediamine |
| 11 | 2-fluoro-11,12-dihydropyrido[2,1-b][1,3]benzodiazepine | 2-[di-(2-hydroxyethyl)amino]ethyl chloride | 1,1-di-(5-hydroxyethyl)-2-[4-fluoro-2-[2-(1-piperidinyl)ethyl]phenyl]-1,2-ethanediamine |
| 12 | 2-(diethylamidosulfonyl)-11,12-dihydropyrido[2,1-b][1,3]benzodiazepine | 3-(dimethylamino)-propyl chloride | 1,1-dimethyl-3-[5-(diethylamidosulfonyl)-2-[2-(1-piperidinyl)ethyl]phenyl-1,3-propanediamine |
| 13 | 1-fluoro-11,12-dihydropyrido[2,1-b][1,3]benzodiazepine | 4-(ethylamino)-butyl chloride | 1-ethyl-4-[6-fluoro-2-[2-(1-piperidinyl)ethyl]phenyl]-1,4-butanediamine |
| 14 | 3-sulfamoyl-11,12-dihydropyrido[2,1-b][1,3]benzodiazepine | 2-(propylamino)-ethyl chloride | 1-propyl-2-[4-sulfamoyl-2-[2-(1-piperidinyl)ethyl]phenyl]-1,2-ethanediamine |
| 15 | 3-(trifluoromethyl)-11,12-dihydropyrido[2,1-b][1,3]-benzodiazepine | 2-(t-butylamino)-ethyl chloride | 1-t-butyl-2-[4-(trifluoromethyl)-2-[2-(1-piperidinyl)ethyl]phenyl]-1,2-ethanediamine |
| 16 | 2-chloro-11,12-dihydropyrido[2,1-b][1,3]benzodiazepine | 3-(dimethylamino)-propyl chloride | 1,1-dimethyl-3-[5-chloro-2-[2-(1-piperidinyl)ethyl]phenyl]-1,3-propanediamine |
| 17 | 3-(methylthio)-11,12-dihydropyrido[2,1-b][1,3]-benzodiazepine | 2-(dimethylamino)-ethyl chloride | 1,1-dimethyl-2-[4-(methylthio)-2-[2-(1-piperidinyl)ethyl]phenyl]-1,2-ethanediamine |
| 18 | 8-chloro-3-(p-tolyl)-11,12-dihydropyrido[2,1-b][1,3]benzodiazepine | 3-(dimethylamino)-propyl chloride | 1,1-dimethyl-3-[4-(p-tolyl)-2-[2-(3-chloro-1-piperidinyl)ethyl]phenyl]-1,3-propanediamine |
| 19 | 8-bromo-4-[m-(trifluoromethyl)phenyl]-11,12-dihydropyrido[2,1-b][1,3]benzodiazepine | 4-(dimethylamino)-butyl chloride | 1,1-dimethyl-4-[3-[m-(trifluoromethyl)phenyl]-2-[2-(3-bromo-1-piperidinyl)ethyl]phenyl]-1,4-butanediamine |
| 20 | 8-ethyl-4-[p-(methoxy)phenyl]-11,12-dihydropyrido[2,1-b][1,3]benzodiazepine | 2-(diethylamino)-ethyl chloride | 1,1-diethyl-2-[3-[p-(methoxy)phenyl]-2-[2-(3-ethyl-1-piperidinyl)ethyl]phenyl]-1,2-ethanediamine |
| 21 | 2-methyl-11,12-dihydropyrido[2,1-b][1,3]benzodiazepine | 3-[(3-hydroxypropyl)amino]propyl chloride | 1-(3-hydroxypropyl)-2-[5-methyl-2-[2-(1-piperidinyl)ethyl]phenyl]-1,3-propanediamine |
| 22 | 3-(dipropylamidosulfonyl)-11,12-dihydropyrido[2,1-b][1,3]benzodiazepine | 2-(methylamino)-ethyl chloride | 1-methyl-2-[4-(dipropylamidosulfonyl)-2-[2-(1-piperidinyl)ethyl]phenyl]-1,2-ethanediamine |
| 23 | 1-(o-chlorophenyl)-11,12-dihydropyrido[2,1-b][1,3]-benzodiazepine | 3-(dimethylamino)-propyl chloride | 1,1-dimethyl-3-[6-(o-chlorophenyl)-2-[2-(1-piperidinyl)ethyl]phenyl]-1,3-propanediamine |
| 24 | 8-chloro-11,12-dihydropyrido[2,1-b][1,3]benzodiazepine | 4-(dimethylamino)-butyl chloride | 1,1-dimethyl-4-[2-[2-(3-chloro-1-piperidinyl)ethyl]phenyl]-1,4-butanediamine |
| 25 | 6-bromo-11,12-dihydropyrido[2,1-b][1,3]benzodiazepine | 2-(ethylamino)-ethyl chloride | 1-ethyl-2-[2-[2-(3-bromo-1-piperidinyl)ethyl]phenyl]-1,2-ethanediamine |
| 26 | 8-bromo-11,12-dihydropyrido[2,1-b][1,3]benzodiazepine | 2-(diethylamino)-ethyl chloride | 1,1-diethyl-2-[2-[2-(3-bromo-1-piperidinyl)ethyl]phenyl]-1,2-ethanediamine |
| 27 | 6-(ethoxy)-11,12-dihydropyrido[2,1-b][1,3]benzodiazepine | 2-(propylamino)-ethyl chloride | 1-propyl-2-[2-[2-[3-(ethoxy)-1-piperidinyl]ethyl]phenyl]-1,2-ethanediamine |
| 28 | 7-(ethoxy)-11,12-dihydropyrido[2,1-b][1,3]benzodiazepine | 2-(diisopropylamino)ethyl chloride | 1,1-diisopropyl-2-[2-[2-[4-(ethoxy)-1-piperidinyl]ethyl]phenyl]-1,2-ethanediamine |
| 29 | 8-ethyl-11,12-dihydropyrido[2,1-b][1,3]benzodiazepine | 3-(methylamino)-propyl chloride | 1-methyl-3-[2-[2-(3-ethyl-1-piperidinyl)ethyl]phenyl]-1,3-propanediamine |
| 30 | 8-(ethoxy)-11,12-dihydropyrido[2,1-b][1,3]benzodiazepine | 3-(dimethylamino)-propyl chloride | 1,1-dimethyl-3-[2-[2-[3-(ethoxy)-1-piperidinyl]ethyl]phenyl]-1,3-propanediamine |
| 31 | 6-ethyl-11,12-dihydropyrido[2,1-b][1,3]benzodiazepine | 3-(ethylamino)-propyl chloride | 1-ethyl-3-[2-[2-(3-ethyl-1-piperidinyl)ethyl]phenyl]-1,3-propanediamine |
| 32 | 6-butyl-11,12-dihydropyrido[2,1-b][1,3]benzodiazepine | 3-(diethylamino)-propyl chloride | 1,1-diethyl-3-[2-[2-(3-butyl-1-piperidinyl)ethyl]phenyl]-1,3-propanediamine |
| 33 | 9-phenyl-11,12-dihydropyrido[2,1-b][1,3]benzodiazepine | 3-(propylamino)-propyl chloride | 1-propyl-3-[2-[2-(2-phenyl-1-piperidinyl)ethyl]phenyl]-1,3-propanediamine |
| 34 | 8-chloro-11,12-dihydropyrido[2,1-b][1,3]benzodiazepine | 3-(dipropylamino)-propyl chloride | 1,1-dipropyl-3-[2-[2-(3-chloro-1-piperidinyl)ethyl]phenyl]-1,3-propanediamine |
| 35 | 6-benzyl-1-(trifluoromethyl)-11,12-dihydropyrido[2,1-b][1,3]benzodiazepine | 3-(butylamino)-propyl chloride | 1-butyl-3-[2-[2-(3-benzyl-1-piperidinyl)ethyl]phenyl]-1,3-propanediamine |
| 36 | 6-[m-(ethoxy)phenyl]-3-fluoro-11,12-dihydro- | 3-(dibutylamino)-propyl chloride | 1,1-dibutyl-3-[4-fluoro-2-[2-[3-[m-(ethoxy)phenyl]-1-piper- |

-continued

| Example | Column I | Column II | Column III |
|---|---|---|---|
| | pyrido[2,1-b][1,3]benzodiazepine | | idinyl]ethyl]phenyl]-1,3-propanediamine |
| 37 | 1-(trifluoromethyl)-8-[o-(trifluoromethyl)phenyl]-11,12-dihydropyrido[2,1-b][1,3]benzodiazepine | 4-(methylamino)butyl chloride | 1-methyl-4-[6-(trifluoromethyl)-2-[2-[3-[o-(trifluoromethyl)phenyl]-1-piperidinyl]ethyl]phenyl]-1,4-butanediamine |
| 38 | 3-chloro-8-(o-tolyl)-11,12-dihydropyrido[2,1-b][1,3]benzodiazepine | 4-(dimethylamino)butyl chloride | 1,1-dimethyl-4-[4-chloro-2-[2-[3-[o-tolyl)-1-piperidinyl]ethyl]phenyl]-1,4-butanediamine |
| 39 | 8-(phenylthio)-11,12-dihydropyrido[2,1-b][1,3]-benzodiazepine | 4-(ethylamino)butyl chloride | 1-ethyl-4-[2-[2-[3-(phenylthio)-1-piperidinyl]ethyl]phenyl]-1,4-butanediamine |
| 40 | 6-(2-phenylethyl)-11,12-dihydropyrido[2,1-b]-[1,3]benzodiazepine | 4-(diethylamino)butyl chloride | 1,1-diethyl-4-[2-[2-[3-(2-phenylethyl)-1-piperidinyl]ethyl]phenyl]-1,4-butanediamine |
| 41 | 6-(o-bromophenyl)-11,12-dihydropyrido[2,1-b]-[1,3]benzodiazepine | 4-(dipropylamino)butyl chloride | 1,1-dipropyl-4-[2-[2-[3-(o-bromophenyl)-1-piperidinyl]ethyl]phenyl]-1,4-butanediamine |
| 42 | 3-phenyl-11,12-dihydropyrido[2,1-b][1,3]benzodiazepine | 2-(dimethylamino)ethyl chloride | 1,1-dimethyl-2-[4-phenyl-2-[2-(1-piperidinyl)ethyl]phenyl]-1,2-ethanediamine |
| 43 | 3-(o-tolyloxy)-11,12-dihydropyrido[2,1-b][1,3]-benzodiazepine | 3-(dimethylamino)propyl chloride | 1,1-dimethyl-3-[4-(o-tolyloxy)-2-[2-(1-piperidinyl)ethyl]phenyl]-1,3-propanediamine |
| 44 | 2-[m-(ethoxy)phenoxy]-11,12-dihydropyrido-[2,1-b][1,3]-benzodiazepine | 4-(dimethylamino)butyl chloride | 1,1-dimethyl-4-[5-[m-(ethoxy)phenoxy]-2-[2-(1-piperidinyl)ethyl]phenyl]-1,4-butanediamine |
| 45 | 3-[o-(trifluoromethyl)phenoxy]-11,12-dihydropyrido[2,1-b][1,3]benzodiazepine | 2-(ethylamino)ethyl chloride | 1-ethyl-2-[4-[o-(trifluoromethyl)phenoxy]-2-[2-(1-piperidinyl)ethyl]phenyl]-1,2-ethanediamine |
| 46 | 2-(o-bromophenoxy)-11,12-dihydropyrido[2,1-b][1,3]benzodiazepine | 2-(dimethylamino)ethyl chloride | 1,1-dimethyl-2-[5-(o-bromophenoxy)-2-[2-(1-piperidinyl)ethyl]phenyl]-1,2-ethanediamine |

What is claimed is:
1. A compound having the formula

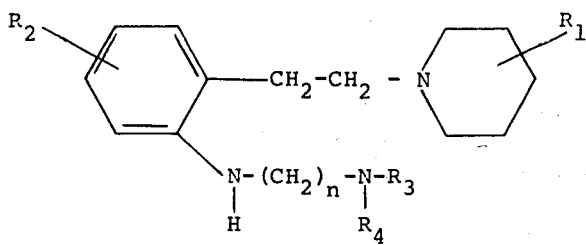

or a pharmaceutically acceptable salt thereof, wherein $R_1$ is hydrogen, halogen, alkyl, alkoxy, alkylthio, benzyl, phenylethyl, phenyl, phenylthio, or phenyl monosubstituted with alkyl, alkoxy or trifluoromethyl; $R_2$ is hydrogen, halogen, alkyl, alkoxy, alkylthio, alkylsulfonyl, phenyl, phenyloxy, sulfamoyl, dialkylamidosulfonyl, trifluoromethyl, or phenyl or phenyloxy mono-substituted with halogen, alkyl, alkoxy or trifluoromethyl; $R_3$ is hydrogen, alkyl or hydroxyalkyl; $R_4$ is alkyl or hydroxyalkyl; and $n$ is 2, 3 or 4; wherein the terms alkyl and alkoxy refer to groups having 1 to 4 carbon atoms.

2. A compound in accordance with claim 1 wherein $R_1$ is hydrogen.

3. A compound in accordance with claim 1 wherein $R_2$ is hydrogen.

4. A compound in accordance with claim 1 wherein $R_1$ and $R_2$ are hydrogen.

5. A compound in accordance with claim 1 wherein $R_3$ is hydrogen.

6. The compound in accordance with claim 1 having the name 1,1-dimethyl-3-[2-[2-(1-piperidinyl)ethyl]phenyl]-1,3-propanediamine.

7. The compound in accordance with claim 1 having the name 1,1-dimethyl-3-[2-[2-(1-piperidinyl)ethyl]phenyl]-1,3-propanediamine, oxalate salt (1:1).

8. The compound in accordance with claim 1 having the name 1,1-dimethyl-2-[2-[2-(1-piperidinyl)ethyl]phenyl]-1,2-ethanediamine.

* * * * *

UNITED STATES PATENT AND TRADEMARK OFFICE
CERTIFICATE OF CORRECTION

PATENT NO. : 3,984,421
DATED : October 5, 1976
INVENTOR(S) : Harry L. Yale et al.

It is certified that error appears in the above—identified patent and that said Letters Patent are hereby corrected as shown below:

In the abstract, line 1 after the formula, "alkylthio" should read -- thereof --.

In the abstract, line 6 after the formula, "Halogen" should read -- halogen --.

In the abstract, line 11 after the formula, "or or " should read -- or --.

In the abstract, line 11 after the formula, please insert after the word "hydroxyalkyl;" the following:

-- $R_4$ is alkyl or hydroxyalkyl; --

Signed and Sealed this

Fifteenth Day of February 1977

[SEAL]

Attest:

RUTH C. MASON
Attesting Officer

C. MARSHALL DANN
Commissioner of Patents and Trademarks